United States Patent
Abrams et al.

[11] Patent Number: 5,411,476
[45] Date of Patent: May 2, 1995

[54] SUPERELASTIC GUIDING MEMBER

[75] Inventors: Robert M. Abrams, Mountain View; Sepehr Fariabi, Fremont, both of Calif.

[73] Assignee: Advanced Cardiovascular Systems, Inc., Santa Clara, Calif.

[21] Appl. No.: 71,322

[22] Filed: Jun. 2, 1993

Related U.S. Application Data

[63] Continuation of Ser. No. 629,381, Dec. 18, 1990, abandoned.

[51] Int. Cl.$^6$ .................................. A61M 37/00
[52] U.S. Cl. .................................. 604/95; 604/96; 604/281; 128/657
[58] Field of Search ............ 604/95, 96, 164, 280–282; 128/657, 658, 772; 606/78, 192, 194; 148/402; 420/902

[56] References Cited

U.S. PATENT DOCUMENTS

| | | | |
|---|---|---|---|
| 3,558,369 | 1/1971 | Wang et al. | 148/11.5 |
| 3,605,725 | 9/1971 | Bentov | 128/205 |
| 3,620,212 | 11/1971 | Fannon et al. | 128/130 |
| 3,890,977 | 6/1975 | Wilson | 128/418 |
| 4,037,324 | 7/1977 | Andreasen | 32/14 |
| 4,233,690 | 11/1980 | Akins | 3/1.5 |
| 4,283,233 | 8/1981 | Goldstein et al. | 148/11.5 |
| 4,411,655 | 10/1983 | Schreck | 604/125 |
| 4,425,908 | 1/1984 | Simon | 128/1 |
| 4,427,000 | 1/1984 | Ueda | 128/6 |
| 4,503,569 | 3/1985 | Dotter | 3/1.4 |
| 4,505,767 | 3/1985 | Quin | 420/441 |
| 4,512,338 | 4/1985 | Balko et al. | 128/1 |
| 4,580,568 | 4/1986 | Gianturco | 128/345 |
| 4,665,906 | 5/1987 | Jervis | 128/92 |
| 4,768,507 | 9/1988 | Fischell et al. | 128/303 |
| 4,776,844 | 10/1988 | Ueda | 604/95 |
| 4,881,981 | 11/1989 | Thoma et al. | 148/11.5 |
| 4,925,445 | 5/1990 | Sakamoto et al. | 604/95 |
| 4,935,068 | 6/1990 | Duerig | 148/402 |
| 4,984,581 | 1/1991 | Stice | 604/95 |
| 4,991,602 | 2/1991 | Amplatz et al. | 604/164 |
| 5,025,799 | 6/1991 | Wilson | 604/95 |
| 5,067,957 | 11/1991 | Jervis | 606/78 |
| 5,069,226 | 12/1991 | Yamauchi et al. | 604/95 |
| 5,120,308 | 6/1992 | Hess | 128/772 |

FOREIGN PATENT DOCUMENTS

| | | |
|---|---|---|
| 55-164304 | 11/1980 | Japan. |
| 9013329 | 11/1990 | WIPO ................ 604/281 |

Primary Examiner—John D. Yasko
Attorney, Agent, or Firm—Crosby, Heafey, Roach & May

[57] ABSTRACT

An improved guiding member for advancing a catheter within a body lumen having a unique combination of superelastic characteristics. The superelastic alloy material has a composition consisting of titanium and nickel and may have one or more elements selected from the group consisting of iron, cobalt, vanadium and copper. The alloy material is cold worked and then heat treated at a temperature well above the austenite-to-martensite transformation temperature, while being subjected to longitudinal stresses equal to about 5 to about 50% of the room temperature yield stress to impart to the metal a straight "memory". The guiding member using such improved material exhibits a stress-induced austenite-to-martensite phase transformation at an exceptionally high constant yield strength of at least 90 ksi for solid members and at least 70 ksi for tubular members with a broad recoverable strain of at least about 4% during the phase transformation.

28 Claims, 1 Drawing Sheet

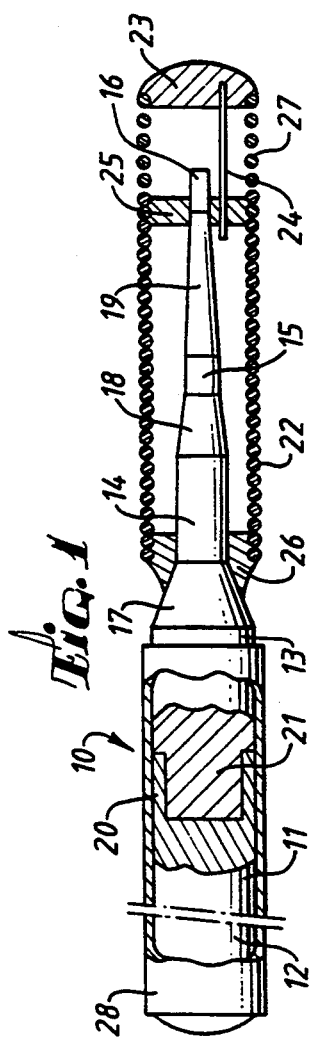
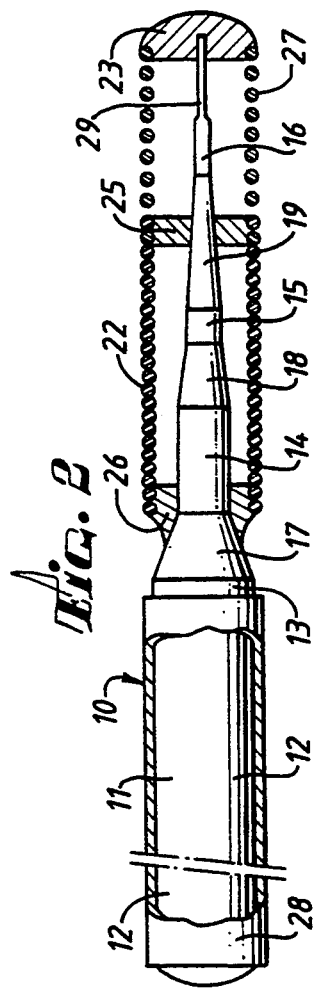
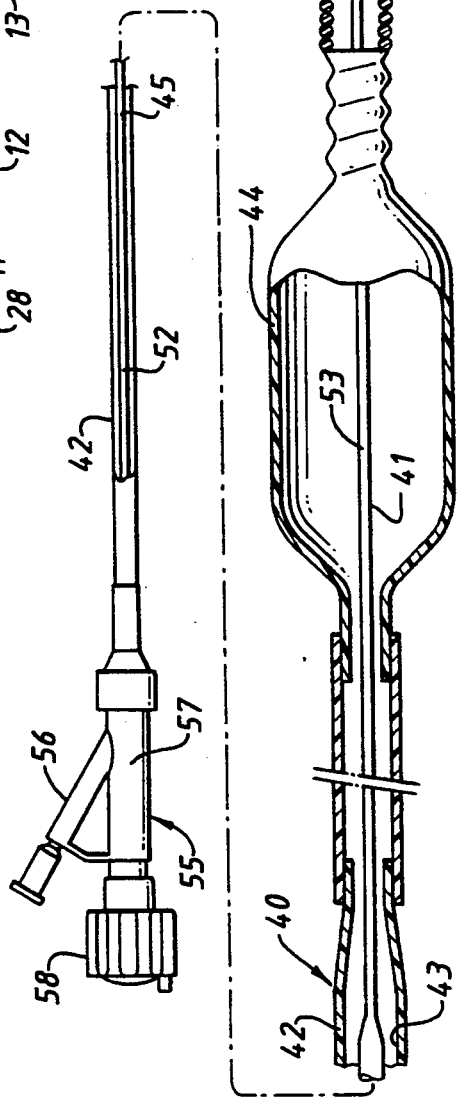
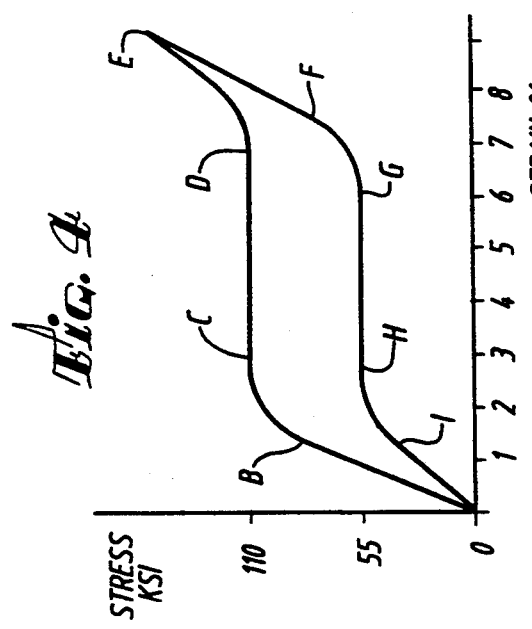

SUPERELASTIC GUIDING MEMBER

This is a continuation of application Ser. No. 07/629,381 which was filed on Dec. 18, 1990, (now abandoned).

BACKGROUND OF THE INVENTION

This invention relates to the field of medical devices, and more particularly to guiding means such as guidewires for advancing catheters within body lumens in procedures such as percutaneous transluminal coronary angioplasty (PTCA).

In typical PTCA procedures a guiding catheter having a preformed distal tip is percutaneously introduced into the cardiovascular system of a patient in a conventional Seldinger technique and advanced therein until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon is inflated to a predetermined size with radiopaque liquid at relatively high pressures (e.g. greater than 4 atmospheres) to compress the arteriosclerotic plaque of the lesion against the inside of the artery wall and to otherwise expand the inner lumen of the artery. The balloon is then deflated so that blood flow is resumed through the dilated artery and the dilatation catheter can be removed therefrom.

Conventional guidewires for angioplasty and other vascular procedures usually comprise an elongated core member with one or more tapered sections near the distal end thereof and a flexible body such as a helical coil disposed about the distal portion of the core member. A shapable member, which may be the distal extremity of the core member or a separate shaping ribbon which is secured to the distal extremity of the core member extends through the flexible body and is secured to a rounded plug at the distal end of the flexible body. Torquing means are provided on the proximal end of the core member to rotate, and thereby steer, the guidewire while it is being advanced through a patient's vascular system.

Further details of dilatation catheters, guidewires, and devices associated therewith for angioplasty procedures can be found in U.S. Pat. No. 4,323,071 (Simpsons-Robert); U.S. Pat. No. 4,439,185 (Lundquist); U.S. Pat. No. 4,516,972 (Samson); U.S. Pat. No. 4,538,622 (Samson et al.); U.S. Pat. No. 4,554,929 (Samson et al.); U.S. Pat. No. 4,616,652 (Simpson); and U.S. Pat. No. 4,638,805 (Powell) which are hereby incorporated herein in their entirety by reference thereto.

Steerable dilatation catheters with fixed, built-in guiding members, such as described in U.S. Pat. No. 4,582,181 (now U.S. Pat. No. Re 33,166) are frequently used because they have lower deflated profiles than conventional over-the-wire dilatation catheters and a lower profile allows the catheter to cross tighter lesions and to be advanced much deeper into a patient's coronary anatomy.

A major requirement for guidewires and other guiding members, whether they be solid wire or tubular members, is that they have sufficient columnar strength to be pushed through a patient's vascular system or other body lumen without kinking. However, they must also be flexible enough to avoid damaging the blood vessel or other body lumen through which they are advanced. Efforts have been made to improve both the strength and flexibility of guidewires to make them more suitable for their intended uses, but these two properties are for the most part diametrically opposed to one another in that an increase in one usually involves a decrease in the other.

The prior art makes reference to the use of alloys such as Nitinol (Ni-Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original undeformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable. The shape of the metal during this heat treatment is the shape "remembered". The heat treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase and during this phase transformation the metal reverts back to its original shape.

The prior methods of using the shape memory characteristics of these alloys in medical devices intended to be placed within a patient's body presented operational difficulties. For example, with shape memory alloys having a stable martensite temperature below body temperature, it was frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices could be introduced into a patient's body with little or no problem, but they had to be heated to the martensite-to-austenite transformation temperature which was frequently high enough to cause tissue damage and very high levels of pain.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation. The martensitic metal first yields elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity.

The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

The Sakamoto et al. patent discloses the use of a nickel-titanium superelastic alloy in an intravascular guidewire which could be processed to develop relatively high yield strength levels. However, at the relatively high yield stress levels which cause the austenite-to-martensite phase transformation characteristic of the material, it did not have a very extensive stress-induced strain range in which the austenite transforms to martensite at relative constant stress. As a result, frequently as the guidewire was being advanced through a patient's tortuous vascular system, it would be stressed beyond the superelastic region, i.e. develop a permanent set or even kink which can result in tissue damage. This permanent deformation would generally require the removal of the guidewire and the replacement thereof with another.

Products of the Jervis patent on the other hand had extensive strain ranges, i.e. 2 to 8% strain, but the relatively constant stress level at which the austenite transformed to martensite was very low, e.g. 50 ksi.

What has been needed and heretofore unavailable is an elongated body for intravascular devices, such as guide wires or guiding members, which have at least a solid or tubular portion thereof exhibiting superelastic characteristics including an extended strain region over a very high, relatively constant high stress level which effects the austenite transformation to martensite. The present invention satisfies this need.

SUMMARY OF THE INVENTION

The present invention is directed to an improved superelastic body which is suitable for intravascular devices, such as guidewires or guiding members, wherein superelastic characteristics result from the stress-induced transformation of austenite to martensite.

The superelastic body of the invention exhibits a stress-induced phase transformation at body temperature (about 37° C.) at a stress level above about 70 ksi, preferably above 90 ksi. The complete stress-induced transformation of the austenite phase to the martensite phase causes a strain in the specimen of at least about 4%, preferably over 5%. The region of phase transformation resulting from stress preferably begins when the specimen has been strained about 2 to 3% at the onset of the phase change from austenite to martensite and extends to about 7 to about 9% strain at the completion of the phase change. The stress and strain referred to herein is measured by tensile testing. The stress-strain relationship determined by applying a bending moment to a cantilevered specimen is slightly different from the relationship determined by tensile testing because the stresses which occur in the specimen during bending are not as uniform as they are in tensile testing. There is considerably less change in stress during the phase transformation than either before or after the stress-induced transformation. In some instances the stress level is almost constant.

The elongated portion of the guiding member having superelastic properties is preferably formed from an alloy consisting essentially of about 40 to 49% titanium and the balance nickel and up to 10% of one or more additional alloying elements. Such other alloying elements may be selected from the group consisting of up to 3% each of iron, cobalt and chromium and up to about 10% copper and vanadium. As used herein all references to percent composition are atomic percent unless otherwise noted.

To form the elongated superelastic portion of the guiding member, elongated solid rod or tubular stock of the preferred alloy material is first cold worked, preferably by drawing, to effect a size reduction of about 30% to about 70% in the transverse cross section thereof. The cold worked material may then be given a memory imparting heat treatment at a temperature of about 350° to about 600° C. for about 0.5 to about 60 minutes, while maintaining a longitudinal stress on the elongated portion equal to about 5% to about 50%, preferably about 10% to about 30%, of the yield stress of the material (as measured at room temperature). This thermomechanical processing imparts a straight "memory" to the superelastic portion and provides a relatively uniform residual stress in the material. Another method involves mechanically straightening the wire after the cold work and then heat treating the wire at temperatures between about 300 degrees and 450 degrees C., preferably about 330 degrees to about 400 degrees C. The latter treatment substantially higher tensile properties. The cold worked and heat treated alloy material has an austenite finish transformation temperature less than body temperature and generally about −10° to about 30° C. For more consistent final properties, it is preferred to fully anneal the solid rod or tubular stock prior to cold work so that the material will always have the same metallurgical structure at the start of the cold working and so that it will have adequate ductility for subsequent cold working. It will be appreciated by those skilled in the art that means of cold working the metal other than drawing, such as rolling or swaging, can be employed. For example, superelastic wire material of the invention will have a constant stress level usually above 90 ksi, whereas, superelastic tubing material will have a constant stress level of above 70 ksi. The ultimate tensile strength of both forms of the material is well above 200 ksi with an ultimate elongation at failure of about 15%.

The elongated body of the invention exhibits a stress-induced austenite-to-martensite phase transformation over a broad region of strain at a very high, relatively constant stress levels. As a result a guiding member formed of this material is very flexible, it can be advanced through very tortuous passageways such as a patient's coronary vasculature with little risk that the superelastic portion of the guiding member will develop a permanent set and at the same time it will effectively transmit the torque applied thereto without causing the guiding member to whip.

These and other advantages of the invention will become more apparent from the following detailed description thereof when taken in conjunction with the following exemplary drawings.

BRIEF DESCRIPTION OF THE DRAWINGS

FIG. 1 illustrates a guidewire which embodies features of the invention.

FIG. 2 illustrates another embodiment of a guidewire of the invention.

FIG. 3 is a partial side elevational view, partially in section, of a guiding member embodying features of the invention which is incorporated into a fixed-wire dilatation catheter adapted for balloon angioplasty procedures.

FIG. 4 is a schematic, graphical illustration of the stress-strain relationship of superelastic material.

DETAILED DESCRIPTION OF THE INVENTION

FIG. 1 illustrates a guidewire 10 embodying features of the invention that is adapted to be inserted into a body lumen 'such as an artery. The guidewire 10 comprises an elongated body or core member 11 having an elongated proximal portion 12 and a distal portion 13, at least part of which, preferably the distal portion, is formed of superelastic material of the invention. The distal portion 13 has a plurality of sections 14, 15 and 16 having sequentially smaller diameters with tapered sections 17, 18 and 19 connecting the smaller diameter sections with adjacent sections. The elongated proximal portion 12 is provided with a female distal end 20 which receives the male end 21 of the distal portion 13. The ends 20 and 21 may be press fit together or may be secured together by means such as a suitable adhesive or by welding, brazing or soldering.

A helical coil 22 is disposed about the distal portion 13 and has a rounded plug 23 on the distal end thereof. A shaping ribbon 24 is secured by the proximal end thereof to the distal portion 13 by suitable means such as brazing at location 25 and by the distal end thereof to the rounded plug 23 which is usually formed by welding the distal end of the coil 22 to the distal tip of the shaping ribbon. The coil 22 is also secured to the distal portion 13 of the elongated body 11 at location 25 and at location 26 to the tapered section 17. Preferably, the most distal section 27 of the helical coil 22 is made of radiopaque metal such as platinum or alloys thereof to facilitate the observation of the distal portion of the guidewire while it is disposed within a patient's body.

The exposed portion of the elongated body 11 should be provided with a coating 28 of lubricous material such as polytetrafluoroethylene (sold under the trademark Teflon by du Pont) or other suitable lubricous coatings such as the polysiloxane coatings disclosed in co-pending application Ser. No. 559,373, filed Jul. 24, 1990 which is hereby incorporated by reference.

FIG. 2 illustrates another embodiment of a guidewire which incorporates features of the invention. This embodiment is very similar to the embodiment shown in FIG. 1 except that the entire elongated body 11 is formed of material having superelastic characteristics and the distal portion 13 of the core member 11 extends all the way to the plug 23 and is preferably flattened at its most distal extremity 29 as ribbon 24 in the embodiment shown in FIG. 1. All of the parts of the guidewire shown in FIG. 2 which correspond to the parts shown in FIG. 1 are numbered the same as in FIG. 1.

FIG. 3 illustrates a fixed wire, steerable dilatation catheter 40 which has incorporated therein a guiding member 41 in accordance with the invention. In this embodiment, the catheter 40 includes an elongated tubular member 42 having an inner lumen 43 extending therein and an inflatable, relatively inelastic dilatation balloon 44 on the distal extremity of the tubular member. Guiding member 41 which includes an elongated body 45, a helical coil 46 disposed about and secured to the distal end of the elongated body 45 and a shaping ribbon 50 extending from the distal end of the elongated body to rounded plug 51 at the distal end of the coil 46. The proximal portion 52 of the elongated body 45 is disposed within the inner lumen 43 of the tubular member 42 and the distal portion 53 of the elongated body 45 extends through the interior of the dilatation balloon 44 and out the distal end thereof. The distal end of the balloon 44 is twisted and sealed about the distal portion 53 of the elongated body 45 extending therethrough in a manner which is described in more detail in copending application Ser. No. 521,103, filed May 9, 1990, which is hereby incorporated herein by reference. The helical coil 46 is secured to the distal portion 53 of the elongated body 45 by suitable means such as brazing at location 54 which is the same location at which the shaping ribbon 50 is secured to the elongated body. Preferably, the distal portion 53 of the elongated body 45 is free to rotate within the twisted seal of the distal end of the balloon 44 and means are provided to seal the distal portion 53 therein to allow air to be vented therethrough but not inflation fluid such as shown in U.S. Pat. No. 4,793,350 (Mar et al.). The proximal end of the catheter 40 is provided with a multiple arm adapter 55 which has one arm 56 for directing inflation fluid through the inner lumen 43 and the interior of the balloon 44. The proximal end of the elongated body 45 extends through arm 57 and is secured to the torquing handle 58 which rotates the guiding member within the catheter 40 as the catheter is advanced through a patient's vascular system. The tubular member 42 may be formed of suitable plastic material such as polyethylene or polyimide or metals such as stainless steel or Nitinol. All or at least the distal portion of the tubular member 42 may be formed of the superelastic NiTi type alloy material of the invention.

The elongated body 11 of the guidewire 10 and elongated body 45 of the fixed-wire catheter 40 are generally about 150 to about 200 cm (typically about 175 cm) in length with an outer diameter of about 0.01 to 0.018 inch for coronary use. Larger diameter guidewire and guiding members may be employed in peripheral arteries. The lengths of the smaller diameter sections 14, 15 and 16 can range from about 5 to about 30 cm. The tapered sections 17, 18 and 19 generally are about 3 cm in length, but these too can have various lengths depending upon the stiffness or flexibility desired in the final product. The helical coils 22 and 46 are about 20 to about 40 cm in length, have an outer diameter about the same size as the diameter of the elongated bodies 11 and 45, and are made from wire about 0.002 to 0.003 inch in diameter. The last or most distal 1.5 to about 4 cm of the coil is expanded and preferably made of platinum or other radiopaque material to facilitate the fluoroscopic observation thereof when the guidewire or fixed wire catheter is inserted into a patient. The remaining portion of the coils 22 and 45 may be stainless steel. The transverse cross-section of the elongated bodies 11 and 45 is generally circular. However, the shaping ribbons 24 and 50 and the flattened distal section 29 have rectangular transverse cross-sections which usually have dimensions of about 0.001 by 0.003 inch.

The superelastic guiding member of the invention, whether it is the entire elongated body 11 or 45 or just a portion thereof, is preferably made of an alloy material consisting essentially of about 40 to about 49% titanium and the balance nickel and up to 10% of one or more other alloying elements. The other alloying elements may be selected from the group consisting of iron, cobalt, vanadium and copper. The alloy can contain up to about 10% copper and vanadium and up to 3% of the other alloying elements. The addition of nickel above the equiatomic amounts with titanium and the other identified alloying elements increase the stress levels at which the stress-induced austenite-to-martensite transformation occurs and ensure that the temperature at which the martensite phase transforms to the austenite phase is well below human body temperature so that austenite is the only stable phase at body temperature. The excess nickel and additional alloying elements also help to provide an expanded strain range at very high stresses when the stress induced transformation of the austenite phase to the martensite phase occurs.

A presently preferred method for making the final configuration of the superelastic portion of the guiding member is to cold work, preferably by drawing, a rod or tubular member having a composition according to the relative proportions described above and then heat treating the cold worked product while it is under stress to impart a shape memory thereto. Typical initial transverse dimensions of the rod or the tubular member are about 0.045 inch and about 0.25 inch respectively. If the final product is to be tubular, a small diameter ingot, e.g. 0.25 to about 1.5 inch in diameter and 5 to about 30 inches in length, may be formed into a hollow tube by extruding or by machining a longitudinal center hole therethrough and grinding the outer surface thereof smooth. Before drawing the solid rod or tubular member, it is preferably annealed at a temperature of about 500° to about 750° C., typically about 650° C., for about 30 minutes in a protective atmosphere such as argon to relieve essentially all internal stresses. In this manner all of the specimens start the subsequent thermomechanical processing in essentially the same metallurgical condition so that products with consistent final properties are obtained. Such treatment also provides the requisite ductility for effective cold working.

The stressed relieved stock is cold worked by drawing to effect a reduction in the cross sectional area thereof of about 30 to about 70%. The metal is drawn through one or more dies of appropriate inner diameter with a reduction per pass of about 10 to 50%.

Following cold work, the drawn wire or hollow tubular product is heat treated at a temperature between about 350° and about 600° C. for about 0.5 to about 60 minutes while simultaneously subjecting the wire or tube to a longitudinal stress between about 5% and about 50%, preferably about 10% to about 30% of the tensile strength of the material (as measured at room temperature) in order to impart a straight "memory" to the metal and to ensure that any residual stresses therein are uniform. This memory imparting heat treatment also fixes the austenite-martensite transformation temperature for the cold worked metal. By developing a straight "memory" and maintaining uniform residual stresses in the superelastic material, there is little or no tendency for a guidewire made of this material to whip when it is torqued within a patient's blood vessel.

An alternate method for imparting a straight memory to the cold worked material includes mechanically straightening the wire or tube and then subjecting the straightened wire to a memory imparting heat treatment at a temperature of about 300 to about 450 degrees C., preferably about 330 degrees to about 400 degrees C. The latter treatment provides substantially improved tensile properties, but it is not very effective on materials which have been cold worked above 55%, particularly above 60%. Materials produced in this manner exhibit stress-induced austenite to martensite phase transformation at very high levels of stress but the stress during the phase transformation is not nearly as constant as the previously discussed method. Conventional mechanical straightening means can be used such as subjecting the material to sufficient longitudinal stress to straighten it.

FIG. 4 illustrates an idealized stress-strain relationship of an alloy specimen having superelastic properties as would be exhibited upon tensile testing of the specimen. The line from point A to point B thereon represents the elastic deformation of the specimen. After point B the strain or deformation is no longer proportional to the applied stress and it is in the region between point B and point C that the stress-induced transformation of the austenite phase to the martensite phase begins to occur. There can be an intermediate phase developed, sometimes called the rhombohedral phase, depending upon the composition of the alloy. At point C the material enters a region of relatively constant stress with significant deformation or strain. It is in this region that the transformation from austenite to martensite occurs. At point D the transformation to the martensite phase due to the application of tensile stress to the specimen is substantially complete. Beyond point D the martensite phase begins to deform, elastically at first, but, beyond point E, the deformation is plastic or permanent.

When the stress applied to the superelastic metal is removed, the metal will recover to its original shape, provided that there was no permanent deformation to the martensite phase. At point F in the recovery process, the metal begins to transform from the stress-induced, unstable martensite phase back to the more stable austenite phase. In the region from point G to point H, which is also an essentially constant stress region, the phase transformation from martensite back to austenite is essentially complete. The line from point I to the starting point A represents the elastic recovery of the metal to its original shape.

EXAMPLE

An elongated rod about 0.025 inch in diameter having a composition of 48.5% Ti and 51.5% Ni was drawn at about 1 foot per minute to a final diameter of 0.016 inch, a reduction of about 60%. The cold drawn wire was heat treated at 475° C. for about 2 minutes in argon while being subjected to tension equal to about 25% of the room temperature yield strength and then cooled. Specimens thereof were tensile tested on a Series IX Instron tensile testing machine at room temperature. The constant stress region under load (Line C to D on FIG. 4), where the austenite is transformed to martensite, was at a level of about 107 ksi and the constant stress region without load (Line G to H on FIG. 4), where the unstable martensite transforms back to austenite, was at a level of about 53 ksi. The strain at the start of the constant stress region under load (Point C on FIG. 4) was about 2.5% and the strain at the end of the constant stress region under load (Point D) was about 7%. The load on the specimen was removed at a strain of 8% (Point E on FIG. 4) and the specimen returned to its original shape and size (Point A on FIG. 4) with little or no residual strain along the curve from point E to Point A shown in FIG. 4.

A key feature of the present invention is the capability of maintaining the level of the yield stress which effects the stress induced austenite-to-martensite transformation as high as possible, e.g. above 70 ksi, preferably above 90 ksi, with an extensive region of recoverable strain, e.g. a strain range of at least 4%, preferably at least 5%, which occurs during the phase transformation.

Because of the extended strain range under stress-induced phase transformation which is characteristic of the superelastic material described herein, a guidewire made at least in part of such material can be readily advanced through tortuous arterial passageways. When the guidewire or guiding member of the invention engages the wall of a body lumen such as a blood vessel, it will deform and in doing so will transform the austenite of the superelastic portion to martensite. Upon the disengagement of the guidewire or guiding member, the stress is reduced or eliminated from within the superelastic portion of the guidewire or guiding member and it recovers to its original shape, i.e. the shape "remembered" which is preferably straight. The straight "memory" in conjunction with little or no nonuniform residual stresses within the guidewire or guiding member prevent whipping of the guidewire when it is torqued from the proximal end thereof. Moreover, due to the very high level of stress needed to transform the austenite phase to the martensite phase, there is little chance for permanent deformation of the guidewire or the guiding member when it is advanced through a patient's artery.

The present invention provides guiding members for guidewires and fixed wire catheters which have superelastic characteristics to facilitate the advancing thereof in a body lumen. The guiding members exhibit extensive, recoverable strain resulting from stress induced phase transformation of austenite to martensite at exceptionally high stress levels which greatly minimizes the risk of damage to arteries during the advancement therein.

The superelastic tubular members of the present invention are particularly attractive for use in a wide variety of intravascular catheters, such as fixed-wire catheters wherein the Nitinol hypotubing having superelastic properties may be employed to direct inflation fluid to the interior of the dilatation balloon. In this case a guiding member may be secured to the distal end of the superelastic Nitinol tubing and extend through the interior of the inflatable balloon and out the distal end thereof. The guiding member may also be made of the superelastic Nitinol of the invention.

Superelastic hypotubing generally has been found to have a slightly lower stress level compared to wire when the austenite is transformed to martensite. However, this stress level is above 40 ksi and is usually above 70 ksi.

The Nitinol hypotubing of the invention generally may have an outer diameter from about 0.05 inch down to about 0.006 inch with wall thicknesses of about 0.001 to about 0.004 inch. A presently preferred superelastic hypotubing has an outer diameter of about 0.012 inch and a wall thickness of about 0.002 inch.

While the above description of the invention is directed to presently preferred embodiments, various modifications and improvements can be made to the invention without departing therefrom.

What is claimed is:

1. An intravascular guidewire comprising
   a) an elongated member having a proximal portion and a distal portion and being formed at least in part of a superelastic NiTi alloy in an austenite phase which is stable at a temperature at or below body temperature, which transforms to a martensite phase upon the application thereto of stress at a relatively constant level above about 70 ksi, which exhibits a strain of about 2 to about 8% when sufficient stress is applied to transform the austenite phase to the martensite phase and which has longitudinal residual stresses and a straight memory therein which result from cold working followed by heat treating at a temperature from about 350° to about 600° C. while being subjected to a longitudinal tension of up to 50% of the ultimate tensile strength of the portion;
   b) a flexible body disposed about the distal portion of the elongated member; and
   c) means on the proximal end of the elongated member to torque this member and transmit such torque to the distal end of the guidewire.

2. The guidewire of claim 1 wherein the distal portion of the elongated member terminates short of the distal extremity of the guidewire and a shaping ribbon extends from the distal end of the elongated member to a rounded plug on the distal end of the flexible body.

3. The guidewire of claim 1 wherein the superelastic portion has a straight memory.

4. An elongated superelastic body formed of a NiTi alloy in an austenite phase which is stable at temperatures up to body temperature, which has residual stress at a relatively uniform level, which will transform to a martensite phase upon the application thereto of a stress at a relatively constant level above about 70 ksi and which exhibits a recoverable strain of about 2 to about 8% upon the application of sufficient stress to induce the transformation of the austenite phase to the martensite phase, said body exhibiting a straight memory resulting from cold working, followed by heat treating at a temperature from about 350° to about 600° C. and straightening.

5. The body of claim 4 wherein the body exhibits a strain of at least about 4% upon the application of a stress above 70 ksi.

6. The body of claim 4 wherein the austenite-to-martensite transformation occurs at a relatively constant yield stress above about 90 ksi.

7. The body of claim 4 wherein the alloy consists essentially of about 40 to about 49% titanium and the balance of the alloy being nickel and up to 10% of other alloying elements.

8. The body of claim 7 wherein the other alloying elements are selected from the group consisting of iron, cobalt, vanadium and copper.

9. The body of claim 8 wherein the alloy contains vanadium or copper in amounts up to about 10% and and iron or cobalt in amounts up to about 3%.

10. The body of claim 4 having a distal portion thereof with a plurality of sections which have progressively smaller cross-sections in the distal direction.

11. The body of claim 4 further comprising a flexible member disposed about a distal portion of the body.

12. The body of claim 11 wherein the flexible member is a helical coil with a rounded plug on the distal end thereof.

13. The body of claim 4 wherein a lubricous polymer coating covers at least a portion thereof.

14. A fixed-wire balloon angioplasty catheter comprising:
 a) an elongated catheter body with an inner lumen extending therein;
 b) an inflatable balloon on the distal extremity of the catheter body and having an interior in fluid communication with the inner lumen of the catheter body; and
 c) a guiding member extending through the interior of the inflatable balloon and formed at least in part of a NiTi superelastic alloy in an austenite phase which is stable at a temperature at or below body temperature, which has relatively uniform residual stress, which transforms to a martensite phase at a relatively constant stress level above about 70 ksi, which exhibits a strain of about 2 to about 8% upon the application of stress sufficient to induce the austenite phase to transform to the martensite phase and which has a straight memory resulting from cold working and then heat treating at a temperature from about 350° to about 600° C. and straightening.

15. An elongated tubular body suitable for use in a medical device within a human body having a cylindrical wall defining an inner lumen therein which is formed at least in part of a NiTi superelastic alloy in an austenite phase which is stable at a temperature below body temperature, which will transform to a martensite phase upon the application of stress, which will exhibit a recoverable strain of about 2 to about 8% upon the application of stress at a level which transforms the austenite phase to the martensite phase, which has residual stresses therein at relatively uniform level and which has a straight memory resulting from cold working and then heat treating at a temperature from about 350° to about 600° C. and straightening.

16. The tubular body of claim 15 wherein the stress level at which the austenite phase transforms to the martensite phase is above 70 ksi.

17. The tubular body of claim 15 wherein the austenite-to-martensite transformation occurs at a relatively constant yield stress above about 90 ksi.

18. The body of claim 15 wherein the alloy consists essentially of about 40 to about 49% titanium and the balance of the alloy being nickel and up to 10% of other alloying elements.

19. The tubular body of claim 18 wherein the other alloying elements are selected from the group consisting of iron, cobalt, vanadium and copper.

20. The tubular body of claim 19 wherein the alloy contains vanadium or copper in amounts up to about 10% and iron and cobalt in amounts up to about 3%.

21. An elongated body for intravascular devices having a straight memory and residual stress at relatively uniform levels and being formed of a NiTi superelastic alloy in an austenite phase which is stable at a temperature below body temperature, which will transform upon the application of stress at a relatively constant level from the austenite phase to a martensite phase, which exhibits a strain of about 2 to about 8% upon the application of stress at a level sufficient to transform the austenite phase to the martensite phase and which has a straight memory resulting from cold working and then heat treating at a temperature between about 350° and 600° C. while being subjected to a longitudinal tension of up to 50% of the ultimate tensile strength thereof.

22. The body of claim 21 wherein the alloy consists essentially of about 40 to about 49% titanium and the balance of the alloy being nickel and up to 10% of other alloying elements.

23. The elongated body of claim 22 wherein the other alloying elements are selected from the group consisting of iron, cobalt, vanadium and copper.

24. The elongated body of claim 23 wherein the alloy contains vanadium or copper in amounts up to about 10% and the other alloying elements in amounts up to about 3%.

25. The elongated body of claim 21 wherein the stress at which the austenite phase transforms to the martensite phase at a relatively constant level above 70 ksi.

26. The elongated body of claim 21 wherein the body exhibits a strain of at least 5% during the stress induced transformation from the austenite phase to the martensite phase.

27. The tubular body of claim 15 having an outer diameter of about 0.006 to about 0.05 inch and a wall thickness of about 0.001 to about 0.004 inch.

28. A superelastic elongated tubular member having an inner lumen extending therein which is formed of a NiTi alloy, which is in an austenite phase at a temperature at or below body temperature, which at body temperature will transform from the austenite phase to a martensite phase and exhibit a recoverable strain of about 2 to about 8% upon the application of stress above 50 ksi, and which has a straight memory resulting from cold working and then heat treating at a temperature between about 350° and 600° C. while being subjected to a longitudinal tension of up to 50% of the ultimate tensile strength thereof.

* * * * *